United States Patent
Vij et al.

(10) Patent No.: US 8,676,529 B2
(45) Date of Patent: Mar. 18, 2014

(54) SYSTEMS AND METHODS FOR SIMULATION AND SOFTWARE TESTING

(75) Inventors: Rohit Vij, San Diego, CA (US); Douglas K. McClure, San Diego, CO (US); Michael Ekaireb, San Diego, CA (US)

(73) Assignee: Covidien LP, Mansfield, MA (US)

( * ) Notice: Subject to any disclaimer, the term of this patent is extended or adjusted under 35 U.S.C. 154(b) by 485 days.

(21) Appl. No.: 13/017,277

(22) Filed: Jan. 31, 2011

(65) Prior Publication Data

US 2012/0197578 A1    Aug. 2, 2012

(51) Int. Cl.
  *G06F 19/00* (2011.01)
(52) U.S. Cl.
  CPC ...................................... *G06F 19/00* (2013.01)
  USPC ....................................................... 702/113
(58) Field of Classification Search
  USPC .......................... 702/113, 117, 118, 182–185
  See application file for complete search history.

(56) References Cited

U.S. PATENT DOCUMENTS

| | | | |
|---|---|---|---|
| 3,734,091 A | 5/1973 | Taplin | |
| 4,479,493 A | 10/1984 | Bung et al. | |
| 4,752,089 A | 6/1988 | Carter | |
| 4,917,080 A | 4/1990 | Bayerlein | |
| 4,921,642 A | 5/1990 | LaTorraca | |
| 4,932,402 A | 6/1990 | Snook et al. | |
| 4,954,799 A | 9/1990 | Kumar | |
| 5,057,822 A | 10/1991 | Hoffman | |
| 5,072,737 A | 12/1991 | Goulding | |
| 5,101,819 A | 4/1992 | Lane | |
| 5,150,291 A | 9/1992 | Cummings et al. | |
| 5,161,525 A | 11/1992 | Kimm et al. | |
| 5,237,987 A | 8/1993 | Anderson et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |
| 5,319,540 A | 6/1994 | Isaza et al. | |
| 5,325,861 A | 7/1994 | Goulding | |
| 5,333,606 A | 8/1994 | Schneider et al. | |
| 5,335,654 A | 8/1994 | Rapoport | |
| 5,339,807 A | 8/1994 | Carter | |
| 5,343,857 A | 9/1994 | Schneider et al. | |
| 5,351,522 A | 10/1994 | Lura | |
| 5,357,946 A | 10/1994 | Kee et al. | |
| 5,368,019 A | 11/1994 | LaTorraca | |
| 5,383,449 A | 1/1995 | Forare et al. | |
| 5,385,142 A | 1/1995 | Brady et al. | |

(Continued)

FOREIGN PATENT DOCUMENTS

| | | |
|---|---|---|
| WO | WO 97/20592 | 6/1997 |
| WO | WO 99/47200 | 9/1999 |
| WO | WO 02/058619 | 8/2002 |

OTHER PUBLICATIONS

7200 Series Ventilator, Options, and Accessories: Operator's Manual. Nellcor Puritan Bennett, Part No. 22300 A, Sep. 1990, pp. 1-196.

(Continued)

*Primary Examiner* — Edward Raymond (57) ABSTRACT

This disclosure describes systems and methods for testing a medical device. The disclosure describes a novel approach determining if the ventilator system is functioning properly without having to connect the medical device to a patient.

18 Claims, 5 Drawing Sheets

(56) References Cited

U.S. PATENT DOCUMENTS

| | | |
|---|---|---|
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,438,980 A | 8/1995 | Phillips |
| 5,443,075 A | 8/1995 | Holscher |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,542,415 A | 8/1996 | Brody |
| 5,544,674 A | 8/1996 | Kelly |
| 5,549,106 A | 8/1996 | Gruenke et al. |
| 5,596,984 A | 1/1997 | O'Mahoney et al. |
| 5,611,335 A | 3/1997 | Makhoul et al. |
| 5,630,411 A | 5/1997 | Holscher |
| 5,632,270 A | 5/1997 | O'Mahoney et al. |
| 5,645,048 A | 7/1997 | Brodsky et al. |
| 5,647,350 A | 7/1997 | Mutch et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,715,812 A | 2/1998 | Deighan et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,878,744 A | 3/1999 | Pfeiffer |
| 5,881,717 A | 3/1999 | Isaza |
| 5,881,723 A | 3/1999 | Wallace et al. |
| 5,884,623 A | 3/1999 | Winter |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,931,160 A | 8/1999 | Gilmore et al. |
| 5,934,274 A | 8/1999 | Merrick et al. |
| 6,024,089 A | 2/2000 | Wallace et al. |
| 6,041,780 A | 3/2000 | Richard et al. |
| 6,047,860 A | 4/2000 | Sanders |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahony et al. |
| 6,158,432 A | 12/2000 | Biondi et al. |
| 6,161,539 A | 12/2000 | Winter |
| 6,220,245 B1 | 4/2001 | Takabayashi et al. |
| 6,269,812 B1 | 8/2001 | Wallace et al. |
| 6,273,088 B1 | 8/2001 | Hillsman |
| 6,273,444 B1 | 8/2001 | Power |
| 6,283,119 B1 | 9/2001 | Bourdon |
| 6,305,373 B1 | 10/2001 | Wallace et al. |
| 6,321,748 B1 | 11/2001 | O'Mahoney |
| 6,325,785 B1 | 12/2001 | Babkes et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,412,483 B1 | 7/2002 | Jones et al. |
| 6,415,791 B1 | 7/2002 | Van Brunt |
| 6,439,229 B1 | 8/2002 | Du et al. |
| 6,463,930 B2 | 10/2002 | Biondi et al. |
| 6,467,478 B1 | 10/2002 | Merrick et al. |
| 6,546,930 B1 | 4/2003 | Emerson et al. |
| 6,553,991 B1 | 4/2003 | Isaza |
| 6,557,553 B1 | 5/2003 | Borrello |
| 6,571,795 B2 | 6/2003 | Bourdon |
| 6,578,575 B1 | 6/2003 | Jonson |
| 6,584,973 B1 | 7/2003 | Biondi et al. |
| 6,622,726 B1 | 9/2003 | Du |
| 6,631,716 B1 | 10/2003 | Robinson et al. |
| 6,644,310 B1 | 11/2003 | Delache et al. |
| 6,668,824 B1 | 12/2003 | Isaza et al. |
| 6,668,829 B2 | 12/2003 | Biondi et al. |
| 6,675,801 B2 | 1/2004 | Wallace et al. |
| 6,688,308 B1 | 2/2004 | Phillips et al. |
| 6,718,974 B1 | 4/2004 | Moberg |
| 6,725,447 B1 | 4/2004 | Gilman et al. |
| 6,739,337 B2 | 5/2004 | Isaza |
| 6,761,167 B1 | 7/2004 | Nadjafizadeh et al. |
| 6,761,168 B1 | 7/2004 | Nadjafizadeh et al. |
| 6,814,074 B1 | 11/2004 | Nadjafizadeh et al. |
| 6,866,040 B1 | 3/2005 | Bourdon |
| 6,960,854 B2 | 11/2005 | Nadjafizadeh et al. |
| 7,017,574 B2 | 3/2006 | Biondi et al. |
| 7,036,504 B2 | 5/2006 | Wallace et al. |
| 7,077,131 B2 | 7/2006 | Hansen |
| RE39,225 E | 8/2006 | Isaza et al. |
| 7,117,438 B2 | 10/2006 | Wallace et al. |
| 7,270,126 B2 | 9/2007 | Wallace et al. |
| 7,334,578 B2 | 2/2008 | Biondi et al. |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,460,959 B2 | 12/2008 | Jafari |
| 7,487,773 B2 | 2/2009 | Li |
| 7,654,802 B2 | 2/2010 | Crawford, Jr. et al. |
| 7,694,677 B2 | 4/2010 | Tang |
| 7,717,113 B2 | 5/2010 | Andrieux |
| D618,356 S | 6/2010 | Ross |
| 7,784,461 B2 | 8/2010 | Figueiredo et al. |
| 7,823,588 B2 | 11/2010 | Hansen |
| 7,855,716 B2 | 12/2010 | McCreary et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0004893 A1 | 6/2001 | Biondi et al. |
| 2002/0026941 A1 | 3/2002 | Biondi et al. |
| 2002/0056452 A1 | 5/2002 | Brewer et al. |
| 2003/0037786 A1 | 2/2003 | Biondi et al. |
| 2004/0055599 A1 | 3/2004 | Strom |
| 2004/0074495 A1 | 4/2004 | Wickham et al. |
| 2004/0079359 A1 | 4/2004 | Aylsworth et al. |
| 2004/0118403 A1 | 6/2004 | O'Connor et al. |
| 2005/0039748 A1 | 2/2005 | Andrieux |
| 2005/0051167 A1 | 3/2005 | Biondi et al. |
| 2005/0066970 A1 | 3/2005 | Donofrio |

(56) References Cited

U.S. PATENT DOCUMENTS

| | | |
|---|---|---|
| 2005/0066971 A1 | 3/2005 | Donofrio |
| 2005/0139212 A1 | 6/2005 | Bourdon |
| 2005/0145248 A1 | 7/2005 | Aylsworth et al. |
| 2006/0162727 A1* | 7/2006 | Biondi et al. ............ 128/204.21 |
| 2006/0254588 A1 | 11/2006 | Brewer et al. |
| 2006/0260611 A1 | 11/2006 | Garber et al. |
| 2006/0283446 A1 | 12/2006 | Chua et al. |
| 2007/0017515 A1 | 1/2007 | Wallace et al. |
| 2007/0077200 A1 | 4/2007 | Baker |
| 2007/0181128 A1 | 8/2007 | Stroetz et al. |
| 2007/0227537 A1 | 10/2007 | Bemister et al. |
| 2007/0277824 A1 | 12/2007 | Aylsworth et al. |
| 2007/0284361 A1 | 12/2007 | Nadjafizadeh et al. |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0320844 A1 | 12/2009 | Nielsen et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197580 A1 | 8/2012 | Vij et al. |

OTHER PUBLICATIONS

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

\* cited by examiner

SYSTEMS AND METHODS FOR SIMULATION AND SOFTWARE TESTING

INTRODUCTION

Ventilator systems have long been used to provide supplemental oxygen support to patients. These ventilators typically comprise a source of pressurized oxygen which is fluidly connected to the patient through a conduit. In some systems, ventilators are designed to automatically adjust to changes in a patient's respiration. Care providers often rely on these automatic adjustments for proper patient care.

Further, other medical devices, such as a pulse oximeter, are also designed to automatically adjust or respond to changes in a patient. Care providers often rely on these automatic adjustments or responses for proper patient care as well.

Because medical devices, such as ventilators, often provide life sustaining functions, a malfunctioning medical device could cause serious problems in patient care. Accordingly, a system or method for checking the function of a medical device is desirable.

SUMMARY

This disclosure describes systems and methods for testing a medical device. The disclosure describes a novel approach determining if the ventilator system is functioning properly without having to connect the medical device to a patient.

In part, this disclosure describes a method for testing a ventilator system. The method includes performing the following steps:

a) sending simulation commands from a simulation system via a software module to a central processing unit on a ventilator system, thereby causing the central processing unit to generate response data and transmit the response data to a controller on the ventilator system;

b) sending an overwrite command that causes the software module to overwrite at least one of monitored data sent to the central processing unit from a breath delivery system and operator input with simulation data based on the simulation commands;

d) intercepting the response data, prior to delivery of the response data to the controller, from the central processing unit based on the simulation commands via the software module;
and e) rerouting the response data to the simulation system via the software module based on the simulation commands.

Yet another aspect of this disclosure describes a ventilator-testing device system that includes: a ventilator system and a testing device. The ventilator system includes:

a) a breath delivery system, the breath delivery system includes hardware components that control gas flow from a gas supply to a patient and control ventilator parameters;

b) a central processing unit that generates commands for the breath delivery system in response to at least one of received data and operator input; and c) a software module, wherein the software module sends simulation data based on received simulation commands to the central processing unit instead of the monitored data sent by the breath delivery system to the central processing unit and receives the response data generated by the central processing unit in response to the simulation data. The hardware components include at least one sensor, the at least one sensor monitors at least one of patient data and breath delivery system data to form monitored data. The testing device includes:

a) a ventilator electrical connection device that electrically connects a ventilator to the testing device;

b) a controller on the testing device that interacts with the software module on the ventilator system and sends simulation commands to the software module via the ventilator electrical connection device;

c) a ventilator system reader that receives response data from the software module generated by the ventilator system in response to the simulation commands, wherein the ventilator system generates the response data by analyzing simulation data generated in response to the simulation commands as if the simulation data were monitored data derived from the hardware within the ventilator system; and d) a compare module in communication with the ventilator system reader, the compare module compares the response data with expected ventilator system response data.

In yet another aspect, the disclosure describes system for simulating sensor data for testing a ventilator system that includes: means for sending simulation commands from a simulation system via a software module to a central processing unit on a ventilator system, thereby causing the central processing unit to generate response data and transmit the response data to a controller on the ventilator system; means for sending an overwrite command that causes the software module to overwrite at least one of monitored data sent to the central processing unit from a breath delivery system and operator input with simulation data based on the simulation commands; means for intercepting the response data, prior to delivery of the response data to the controller, from the central processing unit based on the simulation commands via the software module; and means for rerouting the response data to the simulation system via the software module based on the simulation commands.

In an additional aspect, the disclosure describes a computer-readable medium having computer-executable instructions for performing a method for simulating sensor data for testing a ventilator system. The method includes the following steps:

a) repeatedly sending simulation commands from a simulation system via a software module to a central processing unit on a ventilator system, thereby causing the central processing unit to generate response data and transmit the response data to a controller on the ventilator system;

b) repeatedly sending an overwrite command that causes the software module to overwrite at least one of monitored data sent to the central processing unit from a breath delivery system and operator input with simulation data based on the simulation commands;

c) repeatedly intercepting the response data, prior to delivery of the response data to the controller, from the central processing unit based on the simulation commands via the software module;
and d) repeatedly rerouting the response data to the simulation system via the software module based on the simulation commands.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the technology as claimed.

BRIEF DESCRIPTION OF THE DRAWINGS

The following drawing figures, which form a part of this application, are illustrative of embodiments systems and methods described below and are not meant to limit the scope of the technology in any manner, which scope shall be based on the claims appended hereto.

DETAILED DESCRIPTION

Although the systems and method introduced above and discussed in detail below may be utilized on a variety of medical devices, the present disclosure will discuss the utilization of these systems and methods on a medical ventilator for use in providing ventilation support to a human patient. The reader will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to monitor the rate at which breathing gas is supplied to the patient, to monitor the patient, and to monitor other ventilator features. This data may be gathered with sensors. Some ventilators utilize sensor data to change ventilation parameters and settings, such as changes in gas flow, pressure, timing, and other ventilator settings.

Ventilators often provide life sustaining treatment. Accordingly, systems and methods for testing ventilator function are desired to avoid maintenance issues or malfunctions from occurring during patient treatment. Previously, artificial lungs had been utilized to simulate desired patient breaths to test for proper ventilator response. However, the use of an artificial lung provides limited testing scenarios and little precision. Further, other testing methods require specific hardware changes within the ventilator or the use of additional expensive external electronics, which is costly and burdensome to the operator. Further, these previous systems were extremely expensive, limited to specific devices, and took years to develop. Accordingly, economical testing devices and methods as described herein, which provide more precise ventilator testing and allow for the testing of numerous ventilation scenarios on different types of ventilators, are desirable.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software or firmware components described herein as would be understood by those skilled in the art now and hereafter.

Figure 1:
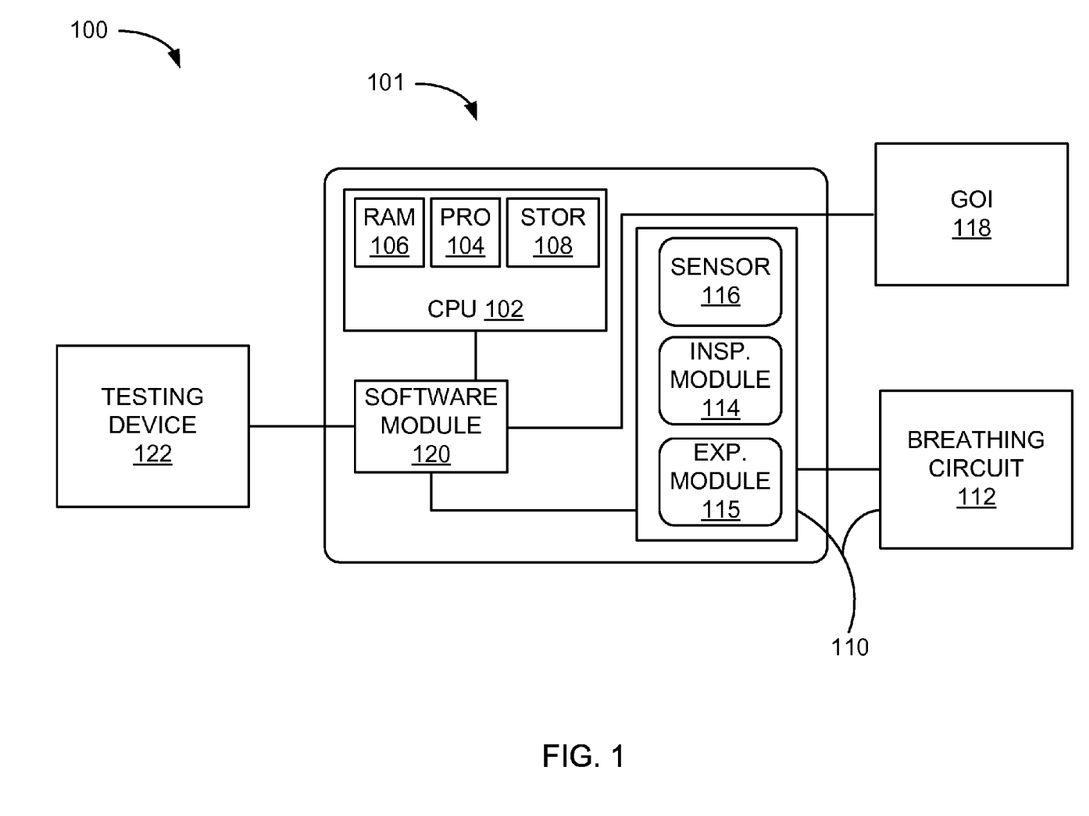
FIG. 1 illustrates an embodiment of a ventilator-testing device system.

FIG. 1 illustrates a ventilator-testing device system 100. The ventilator-testing device system 100 includes a medical ventilator 101 and a testing device 122. The ventilator 101 includes a breath delivery system 110 (also referred to as a pressure generating system) for circulating breathing gases to and from a patient via a ventilation breathing circuit 112, which couples the patient to the ventilator breathing circuit 112 via a physical patient interface. Breath delivery system 110 includes the hardware components for controlling the flow of gas from a gas supply to a patient and for controlling ventilator parameters. The ventilator parameters include any suitable ventilator parameters and/or settings for controlling the ventilation of a patient such as gas mixture, flow rate, pressure, tidal volume, inspiration time, and/or expiration time. This list is exemplary only and is not meant to limit the disclosure.

The breath delivery system 110 has at least one sensor 116. The sensor 116 monitors at least one of patient data and breath delivery system data either or both of which may be referred to as monitored data. The patient data are received from monitoring the patient with a sensor, such as a heart rate sensor or cardiac monitor and/or an oximeter sensor. The breath delivery system data are received from a sensor on the medical ventilator monitoring ventilator parameters, such as a flow sensor and/or carbon dioxide sensor. Any sensor 116 for monitoring the patient or ventilator may be utilized by the ventilator 101.

Breath delivery system 110 may be configured in a variety of ways. The breath delivery system 110 may include an expiratory module 115 coupled with an expiratory limb and an inspiratory module 114 coupled with an inspiratory limb. A compressor or another source or sources of pressurized gas (e.g., pressured air and/or oxygen controlled through the use of one or more gas regulators) may be coupled with the inspiratory module 114 to provide a source of pressurized breathing gas for ventilatory support via the inspiratory limb. Inspiratory module 114 and/or expiratory module 115 may further include gas regulators or valves for controlling the flow of gas through the ventilator breathing circuit 112.

The breath delivery system 110 may include a variety of other hardware components, including sources for pressurized air and/or oxygen, mixing modules, valves, tubing, accumulators, filters, etc. as necessary depending on how the hardware is configured and the capabilities desired.

A ventilator controller 102 or a central processing unit (CPU) 102 communicates through a software module 120 with breath delivery system 110 and a graphical operator interface (GUI) 118. GOI 118 may enable an operator to interact with the ventilator system 101. The CPU 102 may include one or more processors 104, memory 106, storage 108, and/or other components of the type commonly found in command and control computing devices.

The memory 106 is non-transitory or transitory computer-readable storage media that stores software that is executed by the processor and which controls the operation of the medical ventilator 101. In an embodiment, the memory 106 comprises one or more solid-state storage devices such as flash memory chips. In an alternative embodiment, the memory 106 may be mass storage connected to the processor through a mass storage controller (not shown) and a communications bus (not shown). Although the description of non-transitory computer-readable media contained herein refers to a solid-state storage, it should be appreciated by those skilled in the art that non-transitory computer-readable storage media can be any available media that can be accessed by the processor. Non-transitory computer-readable storage media includes volatile and non-volatile, removable and non-removable media implemented in any method or technology for storage of information such as computer-readable instructions, data structures, program modules or other data. Non-transitory computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the processor.

Ventilator 101 and/or breath delivery system 110 may change ventilator settings and parameters based on sensor readings in order to control the breathing assistance provided to the patient by the medical ventilator 101. In an embodiment, the specific changes or commands are determined and sent by CPU 102 and are based on data monitored by the at least one sensor 116 (i.e., the monitored data) and/or inputs received from the graphical operator interface (GOI) 118 of the ventilator 101. In one embodiment, the CPU 102 of the ventilator system 101 fills its internal buffers with analog samples, converts the samples to engineering units, and then continues to process the input (filtering the samples, for example).

Alternatively, CPU 102 may receive simulation commands from the testing device 122. When interpreting/receiving simulation commands from the testing device 122, CPU 102 processes the simulation commands as if it were the monitored data received from physical sensors, operator inputs from the GOI 118, or sampled engineering values from the ventilator system 101.

In one embodiment, just as the CPU 102 runs every 5 msec a pointer into the sent simulation commands would be incremented every 5 msec. In a further embodiment, exact values for the engineering units can be supplied for most parameters/channels in the simulation commands.

Certain advantages of the testing device 122 are that it does not necessarily require any hardware simulations or any additional external electronic device to function; therefore, the inaccuracy of devices such as a digital to analog (d/a) and analog to digital (a/d) converter may be reduced or eliminated.

In the depicted example, the ventilator 110 includes a graphical operator interface (GOI) 118 that includes a display that is touch-sensitive, enabling the GOI 118 to serve both as an input user interface and an output device. In an alternative embodiment, the GOI 118 receives input in addition to and/or solely from another means, such as keyboard, keypad and/or dial. In another embodiment, GOI 118 is merely an output device and does not receive operator information.

The software module 120 of the ventilator 101 is a layer of software on the ventilator 101 that communicates between CPU 102 and breath delivery system 110 and GOI 118. Software module 120 receives the monitored data from sensor 116 and the operator inputs from the GOI 118. Software module 120 selects to send on the monitored data received from the sensor 116 and the operator input received from the GOI 118 to CPU 102 or selects to overwrite the monitored data and the operator input based on simulated commands ands send simulated data to CPU 102. Software module 120 can select to send simulation data from the simulation commands to CPU 102 even if no or only partial monitored data is received from sensor 116 and/or if no or only partial operator inputs are received from the GOI 118. Accordingly, software module 120, CPU 102, and testing device 122 are capable of operating independently of GOI 118 and sensor 116.

In one embodiment, the software module 120 receives the simulation commands from the testing device 122 electrically connected but separate from the ventilator 101. In an embodiment, the simulation commands are selected or input by an operator. In another embodiment, the simulation commands are preset and preconfigured, such as in a test scenario designed to test one or more specific functions of the ventilator 101.

If the software module 120 selects to send on the monitored data received from the sensor 116 and the operator input received from the GOI 118, CPU 102 determines response data for the breath delivery system 110 and GOI 118 based on the monitored data and the operator input and then sends the response data to software module 120 for execution by the various hardware components of the breath delivery system 110. As used herein the term "response data" includes any suitable instructions for the breath delivery system 110 and display information for the GOI 118 based on data received by the CPU 102 from the software module 120. In one embodiment, the response data or instructions includes work of breathing, flow changes, gas mixture changes, alarm setting changes, breath type changes, modes changes, parameter setting changes, etc. This list is exemplary only and is not meant to limit the disclosure.

In one embodiment, software module 120 selects to send the response data to GOT 118 and breath delivery system 110. In another embodiment, software module 120 selects to send the response data to GOI 118, breath delivery system 110, and testing device 122. In an alternative embodiment, software module 120 selects to send the response data to testing device 122 and does not send at least some of the response data to GOI 118 and breath delivery system 110.

If the software module 120 selects to send the response data on to GOI 118 and breath delivery system 110, breath delivery system 110 may utilize the response data from the CPU 102 to change the ventilator parameters for ventilating the patient and GOI 118 may display the sent display information. If the software module 120 selects not to send the response data to GOI 118 and breath delivery system 110, the GOI 118 and breath delivery system 110 continue to operate based on their current settings and/or modes without the response data. In a further embodiment, the software module 120 selects to send the response data to testing device 122 for evaluation.

In one embodiment, the testing device 122 determines if the actual response data are proper based on whether the response data are within an acceptable range or are the same as expected ventilator system response data. As used herein the term "expected ventilator system response data" is an appropriate ventilator response generated in the appropriate amount of time to the simulation data sent by the software module. The response data are appropriate or proper if the response data are within an acceptable range or are the same as the expected ventilator system response data. The response data are not proper if the response data are not within an acceptable range or are not the same as the expected ventilator system response data.

Figure 2:
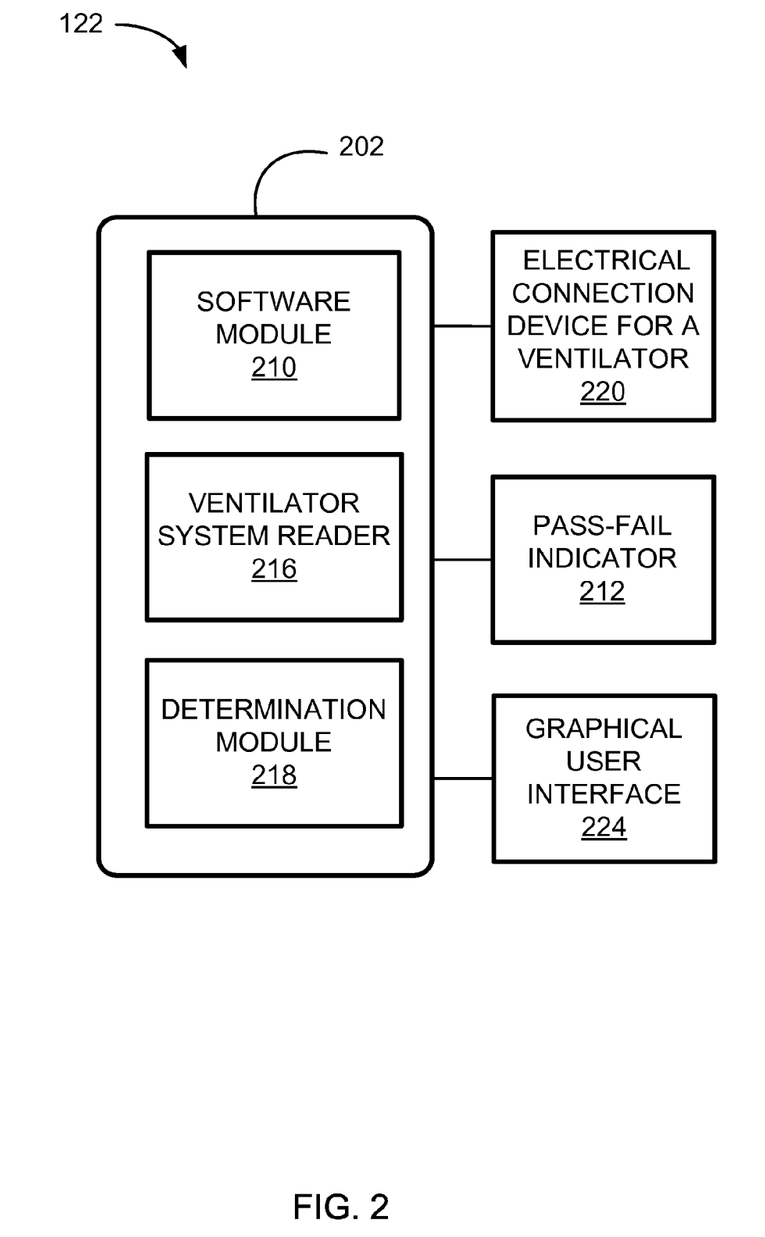
FIG. 2 illustrates an embodiment of a testing device.

FIG. 2 illustrates one embodiment of a testing device 122. In this embodiment, the testing device 122 includes a controller 202, a ventilator electrical connection device 220, a software module 210, a ventilator system reader 216, and a determination module 218. In another embodiment, the testing device 122 further includes a pass-fail indicator 212 and/or a graphical user interface 224. While FIG. 2 is directed to utilizing the testing device 122 on a ventilator system 101, it is understood by a person of skill in the art that the testing device 122 can be adapted for testing any medical device that responds to received patient data and/or operator inputs, such as a pulse oximeter and a capnograph.

The testing device 122 automatically tests a ventilator system 101 to determine if the ventilator system 101 is functioning properly. The testing device 122 tests the functionality of the ventilator system 101 without utilizing an artificial lung or controlling pressure and flow monitored by the ventilator 101 and without making any hardware changes to the ventilator system 101. Further, the testing device 122 does not require the use of any additional external electrical devices, such as d/a converter, an additional electrical interface, voltage converter, external sensors, emulation hardware, and an optical character recognition system. This list is exemplary only and is not meant to limit the disclosure.

The ventilator electrical connection device 220 electrically connects the testing device 122 to the ventilator system 101. In one embodiment, the ventilator electrical connection device 220 electrically connects the controller 202 to the software module 120 of the ventilator system 101. The ventilator electrical connection device 220 allows data, commands, instructions, and/or information (e.g. simulation commands and/or response data) to pass between the testing device 122 and the ventilator system 101 when the ventilator electrical connection device 220 is connected to ventilator system 101.

In one embodiment, the ventilator electrical connection device 220 allows the testing device 122 to communicate with the ventilator system 101 over a wired network or a wireless network. In another embodiment, the ventilator electrical connection device 220 is a cable connecting two communication ports and may be any suitable connection, such as a USB cable or a wireless connection.

In one embodiment, a software module 210 of the testing device 122 interacts with a software module 120 on the ventilator 101 and sends simulation commands to the software module 120 on the ventilator system 101 via the ventilator electrical connection device 220. The software module 120 on the ventilator system 101 controls all communications between the CPU 202 and the testing device 122, breath delivery system 110, and/or the GOI 118. The simulation commands may be any suitable data for testing the response of a ventilator 101 and/or CPU 202 to received sensor data, operator inputs, patient data, and/or ventilator setting and/or parameters. Accordingly, the simulation commands sent to the ventilator system 101 simulates actual received sensor data, operator inputs, patient data, and/or ventilator setting and/or parameters in the ventilator system 101.

In one embodiment, the simulation commands sent by software module 210 on the testing device 122 simulate a breath parameter, an alarm setting, a power supply setting, a gas supply setting, compressor sensor readings, battery sensor readings, and/or oxygen sensor readings. In an embodiment, the breath parameter is intended to model the changes in pressure and flow resulting from a patient cough or hiccup. In another embodiment, the simulation commands sent by the software module 210 simulate power supply sensor readings and/or flow sensor readings. In one embodiment, the simulation commands simulate different ventilation scenarios, such as severe occlusion in the circuit, high exhaled flow, and/or out of range autozero pressures.

Ventilator system reader 216 records a ventilator system response to simulation commands as response data. In one embodiment, the software module 120 on ventilation system 101 sends the response data to the testing device 122 based on simulation commands sent from the software module 210 on the testing device 122. In another embodiment, the software module 120 on ventilation system 101 sends the response data to the testing device 122 based on commands/instructions sent from the ventilation system reader 216 on the testing device 122. In one embodiment, the response data or response instructions include work of breathing, flow changes, gas mixture changes, alarm setting changes, breath type changes, modes changes, and/or parameter setting changes data. Ventilator system reader 216 receives the response data via the ventilator electrical connection device 220.

Determination module 218 determines if the ventilator system 101 is functioning properly after a predetermined amount of time, number of tests, or number of simulated breaths are recorded by the ventilator system reader 216. The desired number of breaths may be selected by a user, input by a user, or predetermined and preprogrammed into the testing device 122. The determination module 218 determines if the ventilator system 101 is functioning properly by comparing the response data to predetermined expected ventilator system response data for the simulation commands sent to the CPU 102 of the ventilator system 101. The determination module 218 determines if the response data are proper based on whether the response data are within an acceptable range or are the same as the expected ventilator system response data.

If the determination module 218 determines that the response data are not the same as the expected ventilator system response data or are outside an acceptable range, the determination module 218 determines that the ventilator system 101 is not functioning properly. Accordingly, in this embodiment, a pass-fail indicator 212 notifies the user that the ventilator system 101 failed the test performed by the testing device 122 on the ventilator system 101. If the determination module 218 determines that the response data are within an acceptable range or the same as the expected ventilator system response data, the determination module 218 determines that the ventilator system 101 is functioning properly. Accordingly, in this embodiment, the pass-fail indicator 212 notifies the user that the ventilator system 101 passed the test performed by the testing device 122 on the ventilator system 101.

In another embodiment, the testing device 122 sends the appropriate simulation commands to the ventilator 101 to trigger any desired ventilator alarm. In this embodiment, the response data evaluated by the testing device 122 is the execution of an alarm by the ventilator 101 or the absence of an execution of an alarm by the ventilator 101. Accordingly, in this embodiment, the expected ventilator system response data is the execution of an alarm within a predetermined amount of time. Therefore, in this embodiment, if the determination module 218 determines that the ventilator 101 did not execute an alarm in the predetermined amount of time in response to the simulation commands, the determination module 218 determines that the ventilator system 101 is not functioning properly. In this embodiment, if the determination module 218 determines that the ventilator 101 did execute an alarm within the predetermined amount of time in response to the simulation commands, the determination module 218 determines that the ventilator system 101 is functioning properly.

The determination module 218 may also perform more complicated analyses than the simple comparison. Any such analyses from which the response data may be validated or verified to determine the operating condition of the ventilator 101 are contemplated within this technology.

The pass-fail indicator 212 notifies the user/operator if the ventilator system passed or failed the performed test by using any suitable visual, audible, and/or vibrational notification. In one embodiment, the pass-fail indicator 212 is displayed on a display screen and may utilize text, icons, animation, and/or color. Notifications may also include email, text message or other electronic message alerts, hardcopy printouts or the like.

The controller 202 of the testing device 122 is electrically connected to or in communication with the software module 210, ventilator system reader 216, and the determination module 218. Further, the controller 202 is electrically connected to or in communication with the ventilator electrical connection device 220. In another embodiment, the controller 202 is electrically connected to or in communication with the pass-fail indicator 212.

In one embodiment, the controller 202 controls the operation of the pass-fail indicator 212. In another embodiment, the controller 202 controls the software module 210, ventilator system reader 216, and/or the determination module 218. In an additional embodiment, the controller 202 monitors the software module 210, ventilator system reader 216, and/or the determination module 218. Accordingly, the software module 210, ventilator system reader 216, and the determination module 218 may be located within the controller 202 as illustrated in FIG. 2. In an alternative embodiment, not illustrated, the software module 210, ventilator system reader 216, and/or the determination module 218 are individual components of testing device 122 located separate from the controller 202.

Controller 202 may include memory, one or more processors, storage, and/or other components of the type commonly found in command and control computing devices as previously described above.

In one embodiment, the testing device 122 includes a graphical user interface (GUI) 224. The GUI 224 includes a display that is touch-sensitive, enabling the GUI 224 to serve both as an input user interface and an output device. In an alternative embodiment, the GUI 224 receives input in addition to and/or solely from another means, such as keyboard, keypad and/or dial. In another embodiment, GUI 224 is merely an output device and does not receive operator information.

The GUI 224 may display any desirable testing system information or data, such as the simulation commands sent to the ventilator system 101. The GUI 224 may further display any desirable ventilator system data or information, such as the ventilator system response data. In one embodiment, the GUI 224 allows a user to input, select, and/or change the simulation commands. In another embodiment, the GUI 224 allows a user to input, select, and/or change ventilation scenarios, thereby causing the simulation commands to change accordingly. In a further embodiment, the GUI 224 displays the pass-fail indicator 212. In one embodiment, the controller 202 is electrically connected to or in communication with the GUI 224. In another embodiment, the controller 202 controls the GUI 224.

Figure 3:
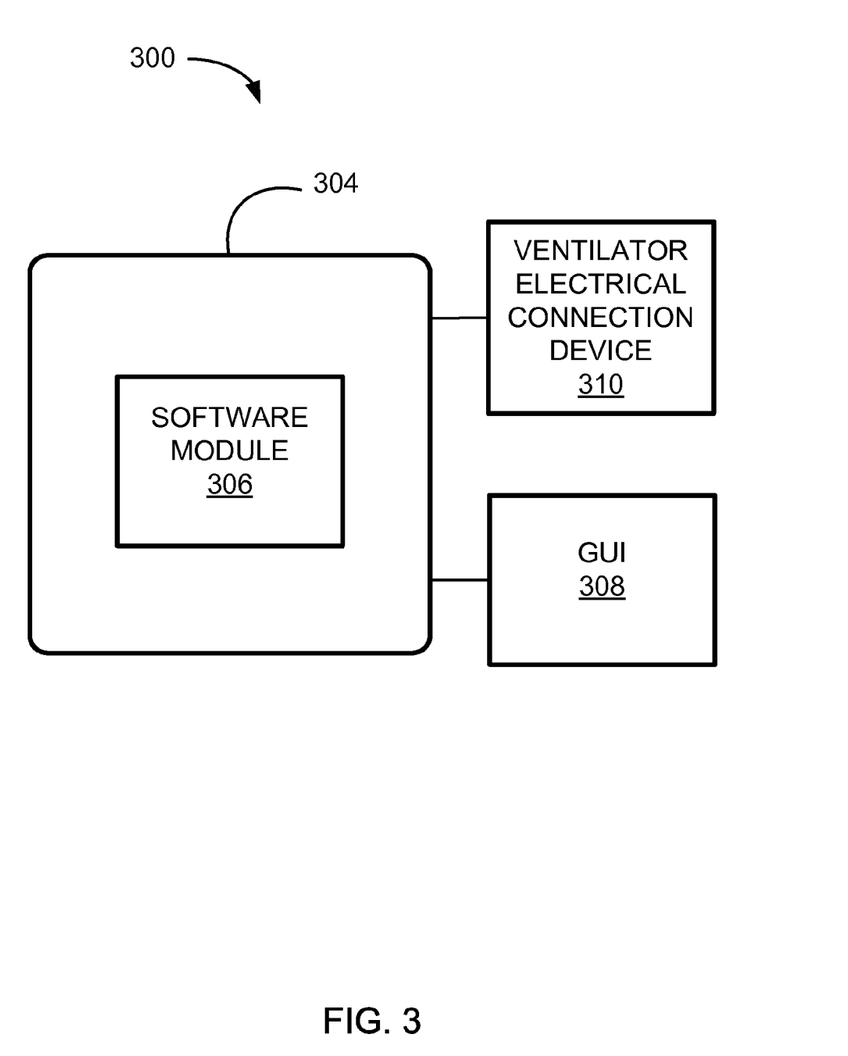
FIG. 3 illustrates an embodiment of a simulation system.

FIG. 3 illustrates an embodiment of a simulation system 300. In one embodiment, testing device 122 illustrated in FIG. 1 functions as the simulation system 300. The simulation system 300 includes a controller 304, a software module 306, and a ventilator electrical connection device 310. In one embodiment, simulation system 300 further includes a GUI 308. While FIG. 3 is directed to use of the simulation system 300 on a ventilator system 101, it is understood by a person of skill in the art that the simulation system 300 can be adapted for testing any medical device that responds to received patient data or operator inputs, such as a pulse oximeter and capnograph.

Controller 304 of the simulation system 300 is electrically connected to or in communication with the software module 306. Further, controller 304 is electrically connected to or in communication with the ventilator electrical connection device 310. In one embodiment, where the simulation system 300 includes a GUI 308, the GUI 308 is electrically connected to or in communication with the controller 304. In another embodiment, the controller controls the GUI 308 and/or the software module 306. As illustrated in FIG. 3, the software module 306 may be located within controller 304. In an alternative embodiment, not shown, the software module 306 is a component separate from controller 304. In one embodiment, controller 304 sends simulation commands/data to the ventilator system through a ventilator electrical connection device 310.

In one embodiment, controller 304 receives response data from the ventilator system 101. The controller 304 could further evaluate the received response data to determine if the ventilator system 101 is functioning properly as defined above. The controller 304 could further generate a pass indicator if the controller determines that the ventilator system 101 is functioning properly. Additionally, the controller 304 could generate a fail indicator if the controller determines that the ventilator system 101 is not functioning properly. In one embodiment, the pass indicator and/or fail indicator is any suitable visual, audio, and/or vibrational notification. In one embodiment, the generated pass indicator or fail indicator is displayed on GUI 308, which may be substantially the same as the GUI 224 described above.

The simulation system 300 tests a ventilator system 101 to determine if the software on the ventilator system 101 is functioning properly. The simulation system 300 sends simulation commands to the software module 120 on the ventilation system 101. Based on the received simulated commands software module 120 generates precise and/or complicated simulated data sent to the ventilator system 101 without connecting an artificial lung to the ventilator system 101 and/or without making any hardware changes to ventilator system 101. Further, the simulation system 300 does not require the use of any additional external electrical devices, such as d/a converter, an additional electrical interface, voltage converter, emulation hardware, external sensors, and an optical character recognition system.

Software module 306 sends simulation commands to the software module 120 on the ventilator system 101 via the ventilator electrical connection device 310 when the ventilator electrical connection device 310 is connected to the ventilator system 101.

As discussed above, the simulation commands, in one embodiment, may simulate patient breaths, coughs, hiccups, and/or any other event for which the performance of the ventilator or any of its subcomponents is to be analyzed. In another embodiment, the simulation commands simulate different ventilation scenarios, such as severe occlusion in the circuit, high exhaled flow, and out of range autozero pressures.

In another embodiment, the simulation system 300 sends a set of "instructions" (or data or commands) that are transmitted from a processor via a JTAG-like process as the simulation commands. This simulation commands or system instructions are sent by the simulation system 300 and are not JTAG operations, instead the controller 304, in this embodiment of the simulation system 300, uses JTAG to transmit instructions or the simulation commands to the module 120 running in the ventilation system 101. As used herein "JTAG" stands for Joint Test Action Group. Background Debug Mode (BDM) and On-Chip Debugging (OCD); are debugging ports. The disclosure refers to a JTAG capability, even though the simulation system 300 may use BDM, OCD, Ethernet or any other known or later developed communication medium.

In one embodiment, typical analog simulation functions or ventilation scenarios of the simulation commands sent by the simulation system 300 are:
  Simulate a pressure spike during inspiration (to trigger a High Ppeak or High Pvent alarm)
  Simulate out-of-range autozero pressures
  Simulate high exhaled flow during exhalation to prolong the Restricted phase of Exhalation
  Simulate low exhaled flow during exhalation to create low tidal volume alarms
  Simulate low pressure during exhalation to trigger an inspiration
  Simulate low pressure during inspiration to prolong a spontaneous inspiration
  Simulate low pressure during inspiration to create a Pcomp alarm
  Simulate pressures to cause or autoreset CIRCUIT DISCONNECT alarms
  Simulate high or low pressures during SEVERE OCCLUSION to shorten or prolong each breath
  Simulate high Pi, Pe pressures to test SEVERE OCCLUSION detection
  Simulate unstable pressures to prolong INSP PAUSE or EXP PAUSE maneuvers
  Simulate out-of-range values for all A/D channels to verify Background/Safety Net checks
  Simulate screen touch on button "set breath rate"
  Simulate knob rotation clockwise/counter clockwise by 5 clicks In another embodiment, typical timing functions or simulation commands sent by the simulation system 300 are:
  Wait for a specified time to elapse
  Wait for the start of inspiration or exhalation
  Wait for an autozero to begin
  Wait for the safety valve to be energized
  Calculate the frequency of LED flashing
  Calculate the frequency of watchdog strobe pulses In an additional embodiment, simulation system 300 sends several digital outputs as simulation commands, such as:
  Set a time tick (set a digital output and record the current time whenever the tick changes state)
  Simulate loss of air or $O_2$ gas supplies (by simulating the gas pressure switches)
  Simulate the presence or absence of the compressor (or simulate compressor failures)
  Set a digital output when the simulation queue becomes empty In one embodiment, the simulation system 300 sends the following simulation commands (or instructions): Deliver a pressure spike in the middle of a simulated inspiration and verify (1) that the inspiration was truncated immediately, but (2) that the breath interval was unchanged. In another embodiment, the scripts in a script-batch file for the previous example include the following:

| | |
|---|---|
| WT4_INSP (1) | #Wait for inspiration to begin; |
| TICK (1) | #Record the current time; |
| WT4_TIME (500) | #Wait for 500 msec; |
| SET_PRESS (PINSP, 60) | #Create a 60 cmH2O pressure spike on Pi; |
| WT4_EXH (0) | #Wait for exhalation; |
| TICK (0) | #Record the current time; |
| WT4_INSP (1) | #Wait for inspiration to begin; and/or |
| TICK (1) | #Record the current time. |

This list is exemplary only is not meant to be limiting.

In another embodiment, the simulation commands sent by the simulation system 300 are digital inputs and outputs. In one embodiment, the simulation system 300 latches the digital channels. In a further embodiment, the simulation commands sent by the simulation system 300 simulates current inputs with the same scheme that simulates voltage inputs.

The software module 306 includes a software component and a hardware component. The software component runs on the CPU 102 of the ventilator system 101. The hardware component communicates between the CPU 102 of the ventilator system 101 and the controller 304 in the simulation system 300.

In one embodiment, the hardware component is an Ethernet interface. In another embodiment, the hardware component is a JTAG hardware interface. In an additional embodiment, the simulation commands are sent to the software component on the CPU 102 via a JTAG interface and saved into simulation queues on the CPU 102. In this embodiment, the simulation commands are a set of interpreter commands that are fetched and executed every 5 msec.

In one embodiment, the instructions/simulation commands sent by the simulation system 300 are interpreted in the CPU 102 and do not require any switchable circuitry or hardware. Previously utilized systems had the ability to simulate analog data, and to force the breath delivery system to sample either the real-world analog inputs or simulated inputs. However, these previous systems require a significant investment in hardware to perform these functions unlike the simulation system 300. For example, unlike the simulation system 300, some previous system required outputs to be sent through d/a converters to perform the simulations.

The software module 120 overwrites monitored data received from components of the ventilator system 101 with simulated data based on simulation commands from the software module 306. The overwriting of monitored data by the software module 120 includes sending simulation data to the CPU 102 even in the absence of monitored data from the components of the ventilator system 101. Accordingly, the CPU 102 generates instructions and/or data (i.e. response data) based on the simulation data from the simulation commands instead of monitored data from the ventilator system 101.

In an alternative embodiment, the testing device 122 is directly integrated in the ventilator system 101 and is a not a separate component or system from the ventilation system 101. In this embodiment, the testing device 122 would be a selectable mode on the ventilator system 101 for testing the ventilator system 101.

Figure 4:
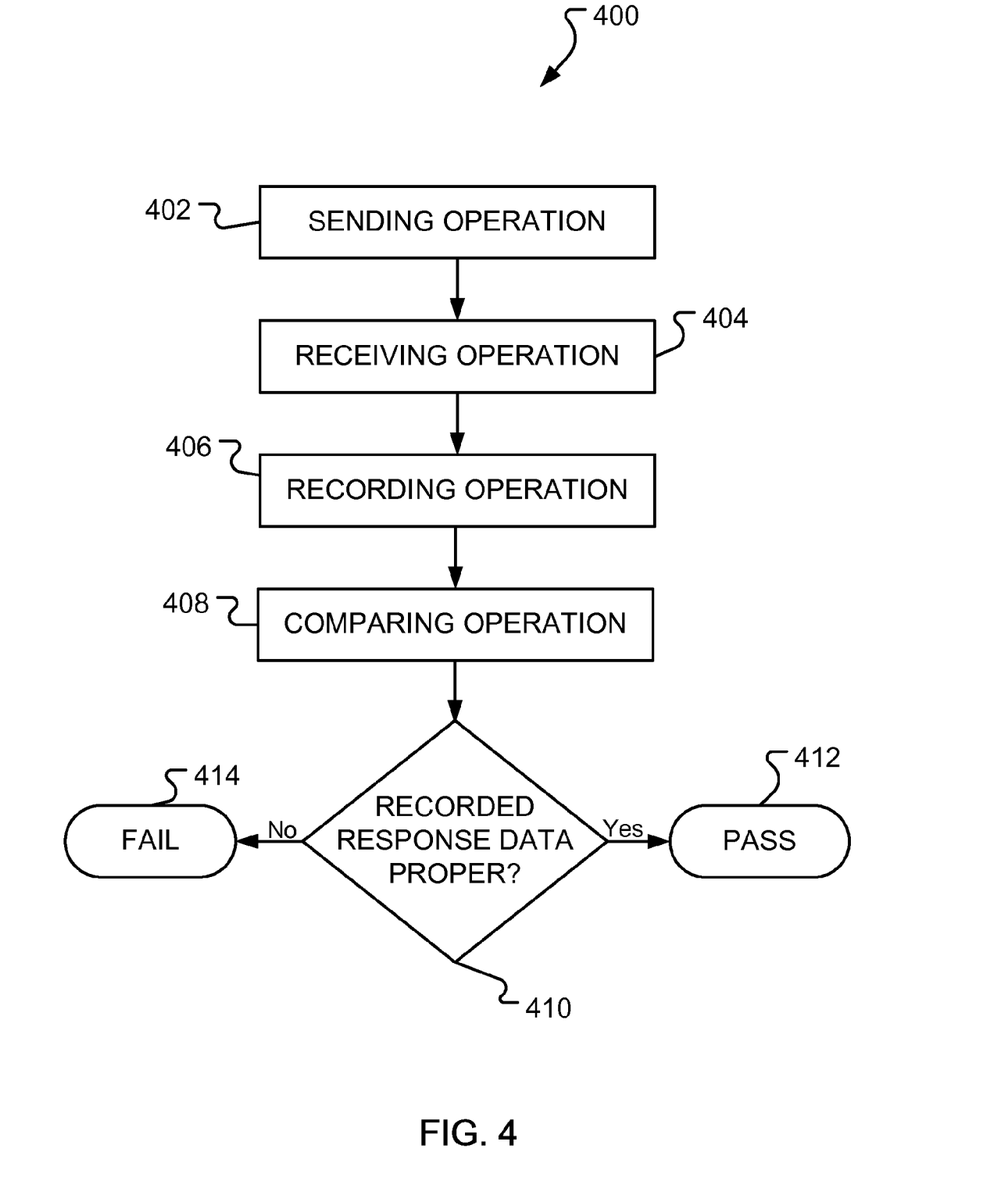
FIG. 4 illustrates an embodiment of a method for testing a ventilator system.

FIG. 4 represents an embodiment of a method 400 for testing a ventilator system. While FIG. 4 is directed to a method of testing a ventilator system, it is understood by a person of skill in the art that this method of testing can be applied to any medical device that responds to received patient data or operator inputs, such as a pulse oximeter and capnograph. As illustrated, method 400 includes sending operation 402. In the sending operation 402, the simulation system transmits simulation commands from a testing device to a ventilator system. In one embodiment, the testing device is electrically connected to ventilator system.

Next, method 400 includes a receiving operation 404. In receiving operation 404, the testing device receives response data from the ventilator system. In one embodiment, the response data are generated by the CPU of the ventilator system. In another embodiment, the response data are sent via an electrical connection formed by a ventilator connection device between a testing device and a ventilation system. The response data includes commands, instruction, and/or data for operating the hardware of the ventilator system.

Further, method 400 includes a recording operation 406. In the recording operation 406, the simulation system records the response data onto the memory of the testing device. In one embodiment, the recording operation 406 is performed by a controller. In another embodiment, the recording operation 406 is performed by a recording module.

Method 400 also includes a comparing operation 408. The ventilator system in comparing operation 408 compares the response data to the expected ventilator system response data. In one embodiment, method 400 may wait to perform comparing operation 408 until recording operation 406 has recorded a predetermined amount of data or the test scenario has completely run (i.e. a test scenario based on desired number of breaths).

Next, method 400 includes a determination operation 410. In determination operation 410, the ventilator system determines if the response data are proper based on whether the response data are within an acceptable range or are the same as expected ventilator system response data. If the determination operation 410 determines that the response data are not within an acceptable range or are not the same as the expected ventilator system response data, determination operation 410 determines that the ventilator system fails the simulation test performed by method 400 and the simulation system executes a fail notification 414. Further, if the determination operation 410 determines that the response data are within an acceptable range or are the same as the expected ventilator system response data, determination operation 410 determines that the ventilator system passes the simulation test performed by method 400 and the simulation system executes a pass notification 412. In one embodiment, the determination operation 412 is performed by a determination module. In another embodiment, the determination operation 412 is performed by a controller.

In one embodiment a pass-fail indicator on the testing device may perform the pass notification 412 and the fail notification 414. The pass-fail indicator may be any suitable type of indicator for notifying a user of whether the ventilator system passed or failed the test performed by method 400, such as an audio, visual, email, SMS text, and/or vibrating notification. In one embodiment, the indicator operation displays the fail notification if the determination operation 410 determines that the response data are not within an acceptable range or are not the same as the expected ventilator system response data. In the same or an alternative embodiment, the indicator operation displays a pass indicator if the determination operation 410 determines that the response data are within an acceptable range or are the same as the expected ventilator system response data.

In an additional embodiment, method 400 further includes a selection operation. In the selection operation of method 400, the testing device receives a selection of user selectable simulation commands, such as simulated sensor readings, ventilation scenarios, ventilator settings, and/or ventilator parameters. Accordingly, in this embodiment, the operator of a testing device is provided with the option of selecting pre-configured simulated sensor readings, ventilation scenarios, ventilator settings, and/or ventilator parameters for the testing of the ventilation system by method 400. This list exemplary only and is not meant to be limiting to the disclosure.

In another embodiment, method 400 includes a display operation. In the display operation of method 400, the testing device displays any desirable testing device information or data. In an embodiment, the desirable testing device information or data includes the simulation commands being sent to the ventilator system. The display operation of method 400 may further display any desirable ventilator system data or information. In one embodiment, the desirable ventilator data or information includes ventilator system response data.

In one embodiment, method 400 is preformed or implemented by the testing device 122 or simulation system 300 as illustrated in FIGS. 1-3 and described above.

Figure 5:
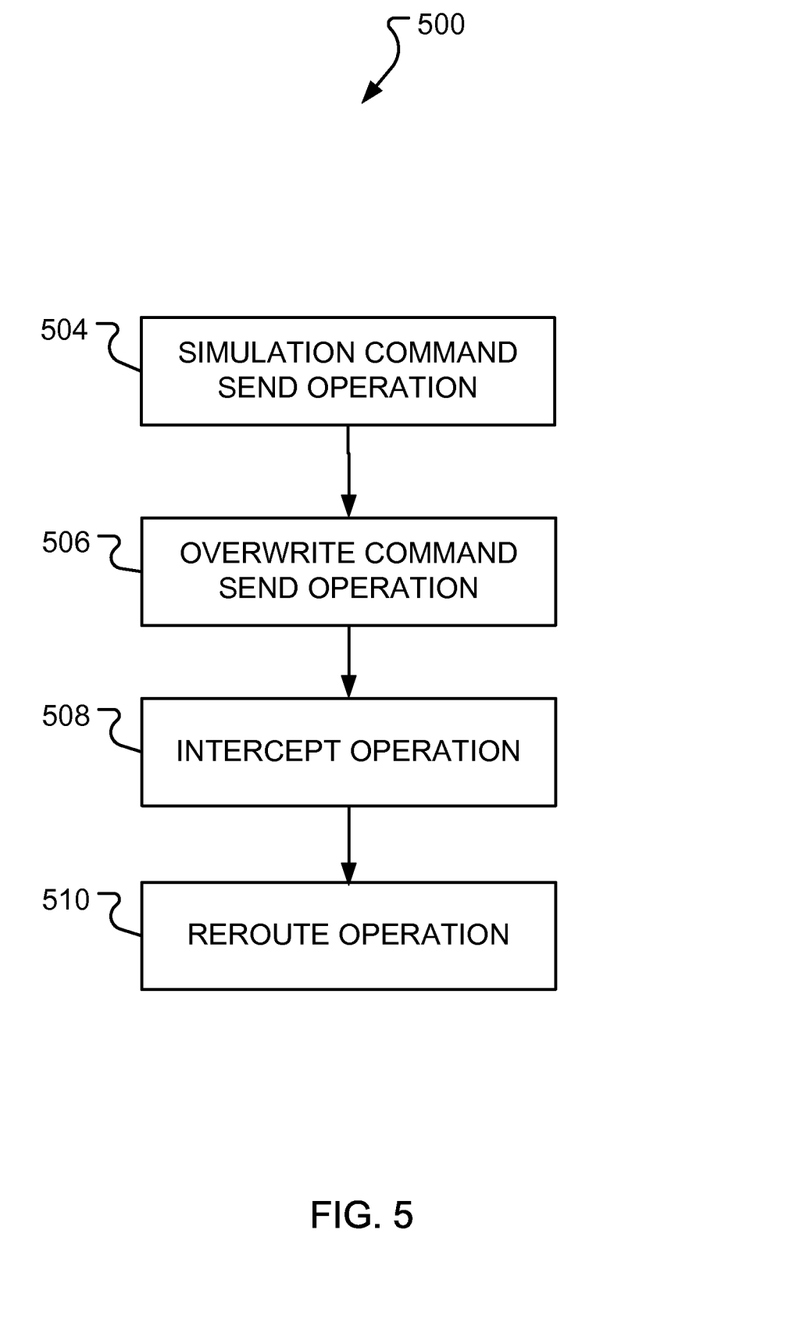
FIG. 5 illustrates an embodiment of a method for testing a ventilator system.

FIG. 5 represents an embodiment of a method 500 for testing a ventilator system. While FIG. 5 is directed to a method of testing a ventilator system, it is understood by a person of skill in the art that this method of testing can be applied to any medical device that responds to received patient data or operator inputs, such as a pulse oximeter and capnograph. As illustrated, method 500 includes a simulation commands send operation 504. In the simulation commands send operation 504, the simulation system transmits simulation data via the software module to the central processing unit on a ventilator system based on sent simulation commands, thereby causing the central processing unit to generate response data and transmit the response data to the software module on the ventilation system. In one embodiment, the software module on the ventilator system controls communication between a central processing unit and a breath delivery system on the ventilator system. Further, in this embodiment, the software module on the ventilator system may control communication between a central processing unit and a GOT on the ventilator system. In one embodiment, simulation commands send operation 504 is performed by a software module and/or controller on a testing device.

Further, method 500 includes an overwrite command send operation 506. In the overwrite command send operation 506, the simulation system sends a command to the software module on the ventilator system to overwrite monitored data from a breath delivery system and/or GOI on the ventilator system with the sent simulation commands. As used herein the phrase "overwrite monitored data" may include, in one embodiment, overwriting the monitored data, replacing the monitored data, not sending the monitored data, utilizing simulated data from simulation commands in the absence of monitor data, and any other suitable process for preventing the monitored data from reaching the CPU or from being processed/analyzed by the CPU. In one embodiment, overwrite command operation 508 is performed by a software module or controller on a testing device.

As illustrated, method 500 includes an intercept operation 508. In the intercept operation 508, the simulation system intercepts response data, such as commands and/or instructions, prior to delivery of the response data to the controller, from the central processing unit based on the simulation commands via the software module. As used herein, the phrase "intercepts response data" may include in one embodiment, any suitable process for controlling what response data, if any, is sent from the CPU of the ventilator system to the breath delivery system or the hardware of the ventilator system. In one embodiment, the intercept operation prevents the response data from being sent to the breath delivery system or hardware of the ventilation system. In another embodiment, the intercept operation sends the response data to the breath delivery system as well as to the simulation system.

Additionally, method 500 includes a reroute operation 510. The simulation system in reroute operation 510, reroutes the response data to the simulation system via the software module. In one embodiment, method 500 records the rerouted response data. In another embodiment, the response data is recorded by a ventilator system reader. In another embodiment, the response data is recorded by a controller.

In another embodiment, method 500 also includes a determination operation. In the determination operation, the simulation system determines if the rerouted response data are proper based on whether the response data are within an acceptable range or are the same as expected ventilator system response data. In one embodiment, method 500 may wait to perform the determination operation until intercept operation 506 has intercepted a predetermined amount of data or the test scenario has completely run, such as a desired number of breaths.

If the determination operation determines that the response data are not within an acceptable range or are not the same as the expected ventilator system response data, determination operation determines that the ventilator system fails the software test performed method 500 and the simulation system executes a fail notification operation. Further, if the determination operation determines that the response data are within an acceptable range or are the same as the expected ventilator system response data, determination operation determines that the ventilator system passes the software test being performed by method 500 and the simulation system executes a pass notification operation. In one embodiment, the determination operation of method 500 is performed by a determination module. In another embodiment, the determination operation of method 500 is performed by a controller.

In one embodiment of method 500, a pass notification operation and a fail notification operation are performed by a pass-fail indicator on the simulation system. The pass-fail indicator notifies the user that the ventilator system being tested by the simulation system passed or failed the test. The pass-fail indicator may be any suitable type of indicator for notifying a user, such as a visual, an audio, an email, an SMS text, and/or a vibration notification. In one embodiment, the indicator displays a fail indicator if the determination operation determines that the response data are not within an acceptable range or are not the same as the expected ventilator system response data. In the same or an alternative embodiment, the indicator displays a pass indicator if the determination operation determines that the response data are within an acceptable range or are the same as the expected ventilator system response data.

In an additional embodiment, method 500 further includes a selection operation. In the selection operation of method 500, the simulation system receives a selection of user selectable simulation commands from the graphical user interface of the simulation system. Accordingly, in this embodiment, the simulation system provides the user with an option to select the simulation commands sent to the ventilator system for software testing the ventilator system.

In another embodiment, method 500 includes a display operation. In the display operation of method 500, the simulation system displays any desirable testing device information or data. In an embodiment, the desirable testing device information or data includes the simulation commands sent to the ventilator system. The display operation of method 500 may further display any desirable ventilator system data or information. In one embodiment, the desirable ventilator system data or information includes ventilator system response data to the simulated sensor data. In one embodiment, method 500 is preformed or implemented by the testing device 122 or simulation system 300 as illustrated in FIGS. 1-3 and described above.

In another embodiment, a computer-readable medium having computer-executable instructions for performing methods for testing a ventilator system and for software testing a ventilator system are disclosed. These methods include repeatedly performing the steps disclosed in method 400 and method 500.

In an additional embodiment, method 400 and method 500 are performed by a ventilator system 101 that has the testing device 122 incorporated into the ventilation system 101. Accordingly, this method is performed entirely by the ventilator system 101 itself and does not include a separate testing device 122. In this embodiment, the simulation testing of the ventilator system 101 would be a selectable mode on the ventilator system 101 for testing the ventilator system 101.

In another embodiment, a testing device is disclosed. The testing device includes means for sending simulation commands to a ventilator system via a testing device electrically connected to the ventilator system, means for receiving a ventilator system response to the simulation commands, means for recording the ventilator system response to the simulation commands as response data on the testing device, and means for comparing the response data to expected ventilator system response data. In one embodiment, the means for the testing device are illustrated in FIGS. 1-3 and described in the above description of FIGS. 1-3. However, the means described above for FIGS. 1-3 and illustrated in FIGS. 1-3 are exemplary only and are not meant to be limiting.

In an additional embodiment, a simulation system is disclosed. The ventilator simulation includes means for sending simulation commands from a simulation system via an software module to a central processing unit on a ventilator system, thereby causing the central processing unit to generate response data and transmit the response data to a controller on the ventilator system, means for intercepting the response data, prior to delivery of the response data to the controller, from the central processing unit based on the simulation commands via the software module, means for sending an overwriting command that causes the software module to overwrite monitored data sent to the central processing unit from a breath delivery system with the simulation commands, and means for rerouting the response data to the simulation system via the software module. In one embodiment, the means for the simulation system are illustrated in FIGS. 1-3 and described in the above descriptions of FIGS. 1-3. However, the means described above for FIGS. 1-3 are exemplary only and are not meant to be limiting.

EXAMPLES

Example 1

In this example, a testing device simulated a patient triggered breath after 200 ms from the start of a previous breath exhalation by utilizing the following commands:

| Simulation Command | Command Description |
| --- | --- |
| simulate Value = PEEP − Psens − 3 | Calculate required pressure value to simulate |
| waitevent (SENSOR_EVENT_START_OF_EXH) | Wait for start of exhalation |
| waittime (200) | Wait 200 ms |
| simulate (SENSOR_EXH_SIDE_PRESSURE_SENSOR, simulateValue) | Set exhalation side pressure sensor value to the value calculated earlier |
| waittime (1) | Wait 1 ms |
| stopsimulate (SENSOR_EXH_SIDE_PRESSURE_SENSOR) | Stop simulation, start sending the actual patient data to the CPU |
| wait_for_breaths ("Assist") | Wait for assist breath generated by the ventilator in response to the simulated low pressure |

The simulation commands sent by the testing device cause the software module to send data to the CPU that simulates sensor values that trick the ventilator into perceiving that a patient is trying to take a breath. The ventilator system in response to this type of a sensor reading should start a new breath of type "Assist". If the ventilator does not start a new "Assist" breath, the ventilator is not functioning properly. However, in this example, the ventilator system did start a new breath. Accordingly, the ventilator system being tested was functioning properly.

Example 2

In this example, a testing device sent the following simulation commands to a ventilator software module as listed below:

| Simulation Command | Command Description |
| --- | --- |
| simulateuserclick ("AC_BUTTON") | select Assist Control mode |
| simulateusersetbuttonvalue ("TIDAL_VOLUME_BUTTON", 500) | set tidal volume to 500 ml |
| simulateuseruserclick ("TRIG_PRESSURE_BUTTON") | set Trigger Type: Pressure |
| simulateusersetbuttonvalue ("ID_RESP_RATE_BUTTON", 6) | set Breath Rate: 6 BPM |
| simulateusersetbuttonvalue ("ID_PEEP_BUTTON", 5) | set PEEP: 5 cmH20 |
| wait_for_breaths (5) | wait for 5 breaths before collecting response data |
| PeakPressure = get_value ("PeakPressure") | receive peak pressure response data from the ventilator |
| BreathRate = get_value ("BreathRate") | Receive breath rate response data from the ventilator |
| TidalVolume = get_value ("TidalVolume") | receive tidal volume response data from the ventilator |

The software module simulated GOI data based on the received simulation commands and sent the simulated data to the CPU. Additionally, the sent simulation commands from the testing device caused the software module to send data to the CPU to simulate different ventilation modes and setting changes. Further, the simulation commands from the testing device caused the software module to send the response data from the CPU to the testing device. The testing device then compared the received response data to expected ventilator response data. The expected ventilator response data utilized for this example is listed below:

A peak pressure between 20 and 30 cm $H_2O$
A breath rate between 3 and 7 bpm; and
A tidal volume between 480 and 520 ml The ventilator system being tested by the testing device sent response data within the ranges listed above. Accordingly, the ventilation system being tested by the testing device in this example passed the test performed by the testing device. The testing device displayed that the ventilation system passed the test or simulation performed by the testing device. If the response data was outside of the expected ventilator response data, the testing device would have found that the ventilator system failed the test performed by the testing device and would have displayed this failure.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present disclosure. Numerous changes may be made which will readily suggest themselves to those skilled in the art and which are encompassed in the spirit of the disclosure and as defined in the appended claims.

What is claimed is:

1. A ventilator-testing device system comprising:
a ventilator system, the ventilator system including:
a breath delivery system, the breath delivery system includes hardware components that control gas flow from a gas supply to a patient and control ventilator parameters,
wherein the hardware components include at least one sensor, the at least one sensor monitors at least one of patient data and breath delivery system data to form monitored data;
a central processing unit that generates and sends response data in response to at least one of the monitored data and operator input, wherein the response data includes commands for the breath delivery system; and
a software module, wherein the software module sends simulation data based on received simulation commands to the central processing unit instead of the monitored data sent by the breath delivery system to the central processing unit and receives the response data generated by the central processing unit in response to the simulation data; and
a testing device, the testing device including:
a ventilator electrical connection device that electrically connects the ventilator system to the testing device;

a controller on the testing device that interacts with the software module on the ventilator system and sends the simulation commands to the software module via the ventilator electrical connection device;

a ventilator system reader that receives the response data from the software module generated by the ventilator system in response to the simulation commands, wherein the ventilator system generates the response data by analyzing the simulation data generated in response to the simulation commands as if the simulation data were monitored data derived from the hardware within the ventilator system; and a compare module in communication with the ventilator system reader, the compare module compares the response data with expected ventilator system response data.

2. A method for testing a ventilator system, the method comprising:

sending simulation commands from a simulation system via a software module to a central processing unit on a ventilator system, thereby causing the central processing unit to generate response data and transmit the response data to a controller on the ventilator system;

sending an overwrite command that causes the software module to overwrite at least one of monitored data sent to the central processing unit from a breath delivery system and operator input with simulation data based on the simulation commands;

intercepting the response data, prior to delivery of the response data to the controller, from the central processing unit based on the simulation commands via the software module;

and rerouting the response data to the simulation system via the software module based on the simulation commands.

3. The method of claim 2, wherein the simulation commands simulate at least one of a breath parameter, an alarm setting, a power supply, a gas supply, a compressor sensor reading, a flow sensor reading, a battery sensor reading, and an oxygen sensor reading.

4. The method of claim 3, wherein the breath parameter simulates at least one of a cough and a hiccup from a patient.

5. The method of claim 2, wherein the simulation commands simulate a ventilator scenario.

6. The method of claim 5, wherein the ventilator scenario simulates severe occlusion in a circuit.

7. The method of claim 5, wherein the ventilator scenario simulates high exhaled flow.

8. The method of claim 7, wherein the ventilator scenario simulates out of range autozero pressures.

9. The method of claim 2, further comprising recording the response data on the simulation system.

10. The method of claim 9, further comprising comparing the response data to expected ventilator system response data.

11. The method of claim 10, further comprising:

determining that the response data is at least one of within an acceptable range and the same as the expected ventilator system response data based on the comparing step; and displaying a pass indicator.

12. The method of claim 10, further comprising:

determining that the response data is at least one of not within an acceptable range and not the same as the expected ventilator system response data based on the comparing step; and displaying a fail indicator.

13. The method of claim 10 further comprising:

displaying the response data on the simulation system.

14. The method of claim 2, further comprising:

displaying the sent simulation commands on the simulation system.

15. The method of claim 2, further comprising:

receiving a selection of user selectable simulation commands from a graphical user interface on the simulation system.

16. The method of claim 2, wherein the software module further controls communication between the central processing unit and a graphical operator interface.

17. A system for simulating sensor data for testing a ventilator system comprising:

means for sending simulation commands from a simulation system via a software module to a central processing unit on a ventilator system, thereby causing the central processing unit to generate response data and transmit the response data to a controller on the ventilator system, wherein the response data includes commands for a breath delivery system;

means for sending an overwrite command that causes the software module to overwrite at least one of monitored data sent to the central processing unit from the breath delivery system and operator input with simulation data based on the simulation commands, wherein the monitored data includes sensor output;

means for intercepting the response data, prior to delivery of the response data to the controller, from the central processing unit based on the simulation commands via the software module;

and means for rerouting the response data to the simulation system via the software module based on the simulation commands.

18. A computer-readable medium having computer-executable instructions for performing a method for simulating sensor data for testing a ventilator system, the method comprising:

repeatedly sending simulation commands from a simulation system via a software module to a central processing unit on a ventilator system, thereby causing the central processing unit to generate response data and transmit the response data to a controller on the ventilator system, wherein the response data includes commands for a breath delivery system;

repeatedly sending an overwrite command that causes the software module to overwrite at least one of monitored data sent to the central processing unit from the breath delivery system and operator input with simulation data based on the simulation commands, wherein the monitored data includes sensor output;

repeatedly intercepting the response data, prior to delivery of the response data to the controller, from the central processing unit based on the simulation commands via the software module; and repeatedly rerouting the response data to the simulation system via the software module based on the simulation commands.

* * * * *